United States Patent
Ahmad et al.

(10) Patent No.: US 7,726,487 B2
(45) Date of Patent: Jun. 1, 2010

(54) COMPLEMENTARY PERSONAL LUBRICANT COMPOSITIONS

(75) Inventors: Nawaz Ahmad, Monmouth Junction, NJ (US); Cheng-Ji Cui, Pennington, NJ (US); Bryant Ison, Lawrenceville, NJ (US); Elysha Huntington, New York, NY (US); Anthony Corwin Yumul, New York, NY (US); Jeffrey Lawrence Jeppesen, New York, NY (US)

(73) Assignee: McNeil-PPC, Inc., Skillman, NJ (US)

( * ) Notice: Subject to any disclaimer, the term of this patent is extended or adjusted under 35 U.S.C. 154(b) by 178 days.

(21) Appl. No.: 11/842,271

(22) Filed: Aug. 21, 2007

(65) Prior Publication Data

US 2008/0194908 A1    Aug. 14, 2008

Related U.S. Application Data

(60) Provisional application No. 60/889,062, filed on Feb. 9, 2007.

(51) Int. Cl.
    *B65D 69/00* (2006.01)
(52) U.S. Cl. .................. 206/568; 206/38; 220/4.24; 220/23.83
(58) Field of Classification Search .............. 206/38, 206/69, 219–222, 568; 220/4.21, 4.24, 23.83, 220/23.87–23.89; 424/43, 47
See application file for complete search history.

(56) References Cited

U.S. PATENT DOCUMENTS

| 4,310,488 A | 1/1982 | Rahm et al. |
| 4,856,647 A * | 8/1989 | Dahne ..................... 206/568 |
| 5,316,159 A * | 5/1994 | Douglas et al. ........... 220/23.83 |
| 5,316,398 A | 5/1994 | Chandaria et al. |
| 6,641,825 B2 | 11/2003 | Scholz et al. |
| 6,929,474 B2 * | 8/2005 | Schenck et al. ............. 206/219 |
| 7,005,408 B2 | 2/2006 | Ahmad et al. |

FOREIGN PATENT DOCUMENTS

| EP | 0 644 129 A | 3/1995 |
| ES | 2 074 030 | 8/1995 |
| JP | 2 311 408 | 12/1990 |

OTHER PUBLICATIONS

Anonymous, "Cambridge Chemistry Set", Jan. 24, 2007 (XP002482987), retrieved from the internet on Jun. 4, 2008: two pages. URL:http://web.archive.org/web/20070124212213/http://www.otherlandtoys.co.uk/cambridge-chemistry-set-p-1759.html.

* cited by examiner

*Primary Examiner*—Luan K Bui
(74) *Attorney, Agent, or Firm*—Karen G. Horowitz (57) ABSTRACT

This invention relates to novel compositions and methods of use by which the compositions of this invention are applied topically to one or more body parts of at least two individuals who bring said body parts into contact with the other individual and, when said body parts come into contact with each other, permit the formulations to interact and thereby achieve an unexpected sensation to each individual.

12 Claims, 3 Drawing Sheets

COMPLEMENTARY PERSONAL LUBRICANT COMPOSITIONS

CROSS-REFERENCE TO RELATED APPLICATIONS

The present application claims the benefit of the earlier filing date of U.S. provisional patent application 60/889,062, filed Feb. 9, 2007, which application is hereby incorporated by reference herein in its entirety, and is related to U.S. patent application Ser. No. 11/842,487, filed on Aug. 21, 2007 pending, which application also claims the benefit of the earlier filing date of provisional patent application 60/889,062.

FIELD OF THE INVENTION

This invention relates to personal lubricant compositions and methods of using such compositions in conjunction with each other by distinct individuals to create new and/or intensified sensations in relation to interpersonal use.

BACKGROUND OF THE INVENTION

Personal lubricant have been sold for decades for the purposes of treating vaginal dryness, for promoting ease of engaging in intimate physical relations and for lubricating diagnostic devices for insertion into body orifices. However, for the last quarter century personal lubricants have achieved an entirely new role in enhancing and making more pleasurable sexual experiences. Personal lubricants have become perceived as a great means to help set the mood for intimate experiences and enhance intimacy. Current personal lubricants may be used by either or both the partners to achieve this goal.

New and more recent additions to this product line are safe, non-irritating warming products that generate warmth when they come into contact with moisture. Examples of such warming personal lubricants are set forth in, for example, U.S. Pat. No. 7,005,408 as well as copending patent applications U.S. Ser. Nos. 10/390,511, 10/389,871, 10/696,939, 10/697,353, 10/697,838, 10/847,082 and 10/847,083, which are hereby incorporated herein by reference.

As intimacy enhancement gains increased focus, substantial number of lubricant products are appearing on the market that work by increasing sensitivity in both males and females by imparting tingling, cooling, numbing or additional unique sensation.

U.S. Pat. No. 6,641,825 B2 of Scholz et al. entitled "Skin Cleansing Gel Having a Heating Effect" describes compositions containing at least 5% by weight of dispersed water-soluble salts with a negative enthalpy of solution, which will release heat upon mixing with water. The compositions also contain anionic, zwiterionic and nonionic surfactants. Such compositions, however, are unsuitable for personal lubricant use as they would be irritating to the delicate mucous membranes of the body.

Japanese Patent Application Number 2-311408, of Akiyama et al., entitled "Gelatinous Compositions for the Skin" sets forth compositions that may contain 0-20% water; solvents such as lower alcohols such as ethanol, isopropanol, propyl alcohol, or organic ethers such as ethyl carbitol, ethyl cellulosolve, chloroform, isopropyl myristate and isopropyl palmitate; and a polyhydric alcohol such as propylene glycol, glycerin, diglycerin and dipropylene glycol. These compositions warm by interacting with water but are unsuitable as personal lubricants because of their irritation potential.

Spanish Patent Number ES2, 074,030 by Manuel Roig Carreras et al., entitled "Self-heating Vehicle Compositions That Can Be Used in Topical Treatments" discusses liquid or semisolid compositions that generate heat by means of an in situ mixing of similar amounts of an aqueous portion (W) consisting mainly of water or an aqueous gel and an organic portion (O) consisting mainly of dimethyl sulfoxide (DMSO), dimethylene glycol or polyethylene glycol. Carreras et al. describes the compositions as being contained in two isolated compartments with adjacent openings that permit simultaneous exit of two parts of self-heating compositions. The compositions of this invention may not be suitable for use as personal lubricants because the DMSO is not suitable for human use and the temperature of the compositions when combined may be too elevated to be safe and comfortable in personal lubricant applications.

The novel compositions and methods of this invention are intended to provide novel sensations to the skin of at least two individuals without being unduly irritating and which interact to provide novel or more intense sensations than each would experience absent the exposure, combination and interaction of the initially-applied compositions to each.

SUMMARY OF THE INVENTION

This invention relates to novel compositions and methods of use by which the compositions of this invention are applied topically to one or more body parts of at least two individuals who bring said body parts into contact with the other individual and, when said body parts come into contact with each other, permit the formulations to interact and thereby achieve an unexpected sensation to each individual. Such sensation may be intensified in relation to the sensation experienced from the initially-applied composition. Alternatively, the sensation experienced by each individual upon combination and interaction of the at least two compositions may be distinctly different from that experienced upon initial application of a first composition. The sensation experienced may alternatively also be an intensification of a sensation of a first composition.

This invention also relates to a unique system for containing and delivering compositions formed in accordance with the present invention. The system provides a container for each composition, and a holder for holding the containers together as a set. The containers may be configured to convey information to consumers as to the concept behind the compositions the containers contain and deliver. For instance, the containers may be in the shape of vials such as test tubes, conveying a sense of experimentation and/or chemical reactions.

DETAILED DESCRIPTION OF PREFERRED EMBODIMENTS

More particularly, this invention relates to a method of creating a sensory result on the skin or mucosa of at least two individuals comprising:

a) applying a first topical composition to the skin or mucosa of at least one first individual;

b) applying a second topical composition to the skin or mucosa of at least one second individual, said second topical composition being different from said first topical composition;

c) bringing the skin of at least one first individual to which said first composition is applied into contact with the skin or mucosa of the second individual to which said second composition is applied; whereby said first and said second topical compositions interact and result in a sensation in each individual. Such compositions may be applied to more than two individuals.

More particularly, this invention also relates to a method of creating a sensory result on the skin or mucosa of at least two individuals comprising:

a) applying a first topical composition to the skin or mucosa of at least one first individual, said first topical composition eliciting a first sensation from said first individual;

b) applying a second topical composition to the skin or mucosa of at least one second individual, said second topical composition being different from said first topical composition and which elicits a second sensation from said second individual;

c) bringing the skin of at least one first individual to which said first composition is applied into contact with the skin or mucosa of the second individual to which said second composition is applied; whereby said first and said second topical compositions interact and result in a sensation in each individual or an intensification of said sensation in said first or said second individual. Such compositions may be applied to more than two individuals.

As used herein, the term "sensation" means an awareness due to stimulation of a sense organ. There are a number of sensations that are known to play a role in enhancing intimate and sexually-related activities. Some have been utilized in conjunction with intimate lubricant compositions in the past to deliver and enhance sexual satisfaction during intimate relationship. The sensation may be a different sensation from that generated by the first topical composition; it may be the same sensation, which is made more intense; or such new sensation may be felt only by one of the partners to which the compositions have been applied. The following are properties or sensations that can be imparted to compositions according to this invention which, when used in accordance with the methods of this invention, convey particular sensations to individuals on whose skin such compositions are placed.

Said compositions may be similar to each other, however they may differ in the proportion of one or more ingredients. Alternatively, they may be different in the type of ingredients present in each compositions. Alternatively, they may contain one or more sensates.

In addition, the compositions and methods of this invention may also include a composition in addition to said first and second compositions that may be useful in halting sensations. Such compositions may include topical analgesics such as lidocaine or benzocaine or the like.

Lubricity or Lubrication

This sensation is one of reduced friction between two surfaces and has been very successfully used in many intimate lubricant products. Lubricant products having higher lubricity helps make sexual relations more physically comfortable, thus eliminating one source of stress in a physical relationship and thereby encouraging intimacy and closeness between the participants. Lubricants or moisturizers may include water-soluble polyhydric alcohols such as propylene glycol, glycerin and polyethylene glycols and the like (others are set forth in U.S. Pat. No. 7,005,408 as well as copending patent applications U.S. Ser. Nos. 10/390,511, 10/389,871, 10/696,939, 10/697,353, 10/697,838, 10/847,082 and 10/847,083, which are hereby incorporated herein by reference.) may be used in aqueous or anhydrous compositions along with glydants like cellulose gums, carbopols and acrylic acid polymers. Silicones are another class of compounds that are very lubricating and may be used to achieve this goal. In addition, other polymers may be used in the compositions and methods of this invention, such as polyquaterniums, polyacrylamides, polysaccharides and the like.

Lubricity may be measured in accordance with the test set forth in U.S. Pat. No. 5,885,591, which is hereby incorporated herein by reference.

Shear-thickening fluids such as polymers that thicken upon combination with other ingredients may be used to generate frictional or tactile sensations. For example, fluids such as corn starch solutions or dispersions or formulations thickened with high levels of polyethylene glycol distearate may thicken and may even gellify under high shear rates.

Frictional or Tactile Sensation

Frictional elements may be useful in the products of this invention to enhance the feeling of touch or tactile sensation that may be preferred by some individuals. In condoms, friction has been successfully employed by condom manufacturers by incorporating ribs and other projections of various forms, size and shape. However these condoms convey the increased sensation only to a female partner. Mechanisms that may contribute to the sensation of friction for a male individual may include the addition of microbeads that can be dispersed in a lubricant compositions. Microbeads are extremely small spheres (approximately 0.2 mm to about 1.6 mm in diameter) composed of cellulose, hydroxypropyl methylcellulose, agar, ALGIN, chitosan materials or a combination thereof, which may be obtained commercially as Primaspheres or Primasponge from Cognis Iberia, Poligon Industrial Saint Vincens, 08755 Castellbisbal, Barcelona, Spain. Addition of microbeads to the compositions of this invention is expected to convey this sensation to be experienced by both partners. Such microbeads may also be constituted such that they are dissolvable in other formulations.

The frictional or tactile sensation may be measured by various computer assisted Tactile Communication Systems specially the ones designed on Braille System by which blinds are able to read foe example TacTapad by Tactiva, 250 W Meadow Drive, Palo Alto, Calif. 94306.

Warming

Warming is a sensation that is associated with closeness and comfort and is measured by the observation of an increase in temperature. It is, therefore, a very positive feeling to bring into an intimate relationship. Warming has been successfully used in anhydrous formulations containing polyhydric alcohols (See, for example, U.S. Pat. No. 7,005,408). The warming sensation may be enhanced if it is used in combination with a non-warming lubricant. Warming and non-warming compositions of this invention may be applied separately to two intimate partners. When the two compositions are combined during the course of sexual intercourse, each partner will experience a sensation of enhanced warmth.

The degree of warming associated with the use of the compositions of applicants' invention may be measured in accordance with the procedures set forth in U.S. Pat. No. 7,005,408, which is hereby incorporated herein by reference.

Cooling

The "cooling" sensation is the opposite of warming, i.e., it is measured by an observation of a decrease in temperature. Cooling is considered an enhancement to intimate relations by some individuals. Cooling sensations may be achieved by including menthol, sorbitol, clohexanecarboxamide, N-methyl-5-methyl-2-(1-methylethyl sold under the trade name Winsense Ws-3, N,2,3-trimethyl-2-isopropyl butamide sold under the trade name Winsense SW-23 and a mixture of these solfd under the trade name Winsense Extra 400 by Millenium Specialty Chemicals Inc., which is a Lyanodell Company. in the compositions of this invention. The cooling sensation may be measured by the use of cooling threshold levels experienced by human subjects. Combining the cooling sensation with another sensation generated by another composition of this invention results in a new, different sensation for both partners utilizing these compositions.

Tingling

"Tingling" is a unique sensation imparted by some chemicals such as methyl salicylate, methyl nicotinate, menthyl lactate and other chemicals. It is defined as "feeling a ringing, stinging, prickling or thrilling sensation" (Webster's Ninth New Collegiate Dictionary, Merriam-Webster, Springfield, Mass., 1987, p. 1236). Compositions that cause the tingling sensation can be used alone or with cooling or warming lubricant compositions to create a novel sensation.

Numbing

"Numbing" is the feeling characterized by the loss of sensation in a particular area of the body. Numbing may be brought about by local anesthetics such as benzocaine, novocaine, lidocaine, tetracainelignocaine, mepivacaine and the like. The numbing feeling may be utilized in compositions applied to a male partner in order to decrease sensitivity of the sexual organs. This can result in a prolongation of intimate physical activities.

Irritation

"Irritation" is a condition of soreness, roughness or inflammation of a body part. Irritants are entities that cause the feeling of irritation. Irritants have been included in sexual lubricant compositions for many years to convey a sensation of soreness or inflammation which may be perceived as aphrodisiac as it increases sensitivity. However, irritation may be perceived as negative or uncomfortable if used in an uncontrolled fashion. We have found that, if used at lower concentrations in accordance with the methods and compositions of this invention, irritants may create a pleasant sensation in the user. Spices such as pepper, capsicum, olive, ginger and cloves and the like and extracts thereof are some examples that may be useful in one or more of the compositions of this invention to create novel sensations in conjunction with other compositions.

Flushing

"Flushing" is the sensation created by enhanced blood flow in a body portion that can cause redness and engorgement of tissues. Engorgement of sexual organs in both females and males is an indication of arousal in both females and males. Certain natural products, such as pepper, chili pepper, ginger and the like may cause such a sensation.

As set forth above, the compositions of this invention are preferably applied in such a way that at least one composition (Composition A) is topically applied to a body part (such as the skin or mucosa) of a first sexual partner and at least one second composition (Composition B) is topically applied to a body part (such as the skin or mucosa) of a second sexual partner. After such application, the partners bring into intimate contact their respective body parts to which the compositions have been applied. The compositions of this invention are designed in such a way as to convey a first sensation when used alone by each partner and a separate, distinct, possibly intensified, sensation when body parts containing Composition A and Composition B are brought into intimate contact with each other.

When the two partners bring their body parts to which the compositions are applied into contact with each other, the compositions mix and interact with each other. The result is the generation of a new sensation or enhancement of the major or the target sensation that is felt or perceived by both partners.

Preferably, the methods of this invention encourage couples in engaging in foreplay, including having one partner applying said first composition to a second partner and said second partner applying said second composition to said first partner. Said method encourages the partners to engage prior to intercourse.

The invention is illustrated by the following examples.

Example 1

Warming Sensation

A first composition as set forth below may be applied to the skin of a first intimate partner. It should convey a feeling of warmth upon application and exposure to ambient moisture in the skin of the first intimate partner. A second composition as set forth below may be applied to the skin of a second partner. This composition is a personal, or sexual, lubricant composition having a high lubricity. The two individuals may bring the skin to which the first and second compositions are applied into contact. Due to the presence of water in the second composition, the combination of the first and second compositions are expected to generate a large increase in temperature.

Such large increase in temperature may be predicted in accordance with the following procedure: 20 ml of each of the ingredients in the First Composition below and the entirety of the First Composition are mixed with 20 ml of the Second Composition. The temperature of the individual ingredient or the First Composition and that of the Second Composition are recorded before the Second Composition is added to the product. After the addition of the Second Composition, the mixture is mixed for two minutes and the actual temperature is recorded. The results of carrying out such a test using the compositions set forth below are as follows:

| Ingredient | % w/w |
|---|---|
| First Composition (Warming) | |
| Propylene Glycol | 25.00 |
| Polyethylene Glycol 400 | 75.00 |
| Total | 100.00 |
| Second Composition (Lubricating) | |
| Polyol | 15.00 |
| Hydroxyalkyl cellulose | 0.75 |
| Preservative | 0.20 |
| Emulsifier | 0.10 |

-continued

| Ingredient | % w/w |
|---|---|
| Antioxidant | 0.01 |
| Water | 83.94 |
| Total | 100.00 |

Warming Results:

Temperature of A: 73° F.

Temperature of B: 71.7° F.

Temperature upon combination: 91.5° F.

Temperature increase upon combination: 19.8° F.

Example 2

Warming Sensation

First and second compositions as set forth below may be first applied to separate partners and then the skin of both partners to which the compositions may be applied were brought into direct contact. This is expected to result in an increased temperature that would be felt by both individuals.

| Ingredient | % w/w |
|---|---|
| First Composition (Warming) | |
| Propylene Glycol | 25.00 |
| Polyethylene Glycol 400 | 75.00 |
| Total | 100.00 |
| Second Composition (Lubricating) | |
| Sorbitol Solution | 20.00 |
| Hydroxyethylcellulose | 0.20 to 0.40 |
| Water | 79.6 to 79.8 |
| Total | 100.00 |

Warming Results:

Temperature of First Composition: 71.6° F.

Temperature of Second Composition: 73.2° F.

Temperature on Mixing: 92.4° F.

Temperature increase upon combination: 20° F.

Example 3

Warming and Tingling Sensation

First and second compositions set forth below may be applied to a first and a second partner as set forth in Examples 1 and 2 above.

| Ingredient | % w/w |
|---|---|
| First Composition (Warming) | |
| Propylene Glycol | 25.00 |
| Polyethylene Glycol 400 | 75.00 |
| Total | 100.00 |

-continued

| Ingredient | % w/w |
|---|---|
| Second Composition (Tingling) | |
| Polyol | 35.00 |
| Cooling Ingredient 1 | 0.05 |
| Cooling Ingredient 2 | 0.05 |
| Cooling Ingredient 3 | 0.04 |
| Sorbitol Solution (70%) | 10.00 |
| Hydroxyalkylcellulose | 0.45 |
| Preservative | 0.20 |
| Emulsifier | 0.10 |
| Water | 54.11 |
| Total | 100.00 |

Upon mixing, the compositions should result in a sensation that is warming plus tingling.

Example 4

Warming and Flushing Sensation

First and second compositions set forth below may be applied to a first and a second partner as set forth in Examples 1 and 2 above.

| Ingredient | % w/w |
|---|---|
| First Composition (Warming) | |
| Propylene Glycol | 25.00 |
| Polyethylene Glycol 400 | 75.00 |
| Total | 100.00 |
| Second Composition (Flushing) | |
| Propylene Glycol | 24.50 |
| Polyethylene Glycol 400 | 75.00 |
| Ginger | 0.50 |
| Total | 100.00 |

Sensation Results:

Both partners should feel warming and flushing.

Example 5

Warming and Numbing Sensations

First and second compositions set forth below may be applied to a first and a second partner as set forth in Examples 1 and 2 above.

| Ingredient | % w/w |
|---|---|
| First Composition (Warming): | |
| Propylene Glycol | 25.00 |
| Polyethylene Glycol 400 | 75.00 |
| Total | 100.00 |

| Ingredient | % w/w |
|---|---|
| Second Composition (Numbing): | |
| Propylene Glycol | 24.50 |
| Polyethylene Glycol 400 | 75.00 |
| Benzocaine | 0.50 |
| Total | 100.00 |

Sensation Results:

Both partners should feel both a warming and a numbing sensation.

Example 6

Warming and Irritation Sensation

First and second compositions set forth below may be applied to a first and a second partner as set forth in Examples 1 and 2 above.

| Ingredient | % w/w |
|---|---|
| First Composition (Warming): | |
| Propylene Glycol | 25.00 |
| Polyethylene Glycol 400 | 75.00 |
| Total | 100.00 |
| Second Composition (Irritant): | |
| Propylene Glycol | 24.50 |
| Polyethylene Glycol 400 | 75.00 |
| Ginger Extract | 0.50 |
| Total | 100.00 |

Sensation Results:

Both partners should feel both a warming and an irritating sensation.

Example 7

Warming and Tactile Sensation

First and second compositions set forth below may be applied to a first and a second partner as set forth in Examples 1 and 2 above.

| Ingredient | % w/w |
|---|---|
| First Composition (Warming) | |
| Propylene Glycol | 25.00 |
| Polyethylene Glycol 400 | 75.00 |
| Total | 100.00 |
| Second Composition (Tactile/Frictional) | |
| Propylene Glycol | 24.50 |
| Polyethylene Glycol 400 | 75.00 |
| Microbeads | 0.50 |
| Total | 100.00 |

Sensation Results:

Both partners should feel a warming sensation and a heightened tactile sense due to friction created with the microbeads.

Example 8

Warming and Tingling Sensation

First and second compositions set forth below may be applied to a first and second partner as set forth in Examples 1 and 2 above.

| Ingredient | % w/w |
|---|---|
| First Composition (Warming) | |
| Polyethylene Glycol 400 | 75.00 |
| Propylene glycol | 24.60 |
| DL-a-Tocopherol | 0.10 |
| Hydroxypropyl cellulose | 0.30 |
| Total | 100.00 |
| Second Composition (Tingling) | |
| Propylene Glycol, USP | 15.00 |
| Natrosol 250H, NF | 0.75 |
| Benzoic Acid, USP | 0.20 |
| Polysorbate 60 | 1.00 |
| Cooling Ingredient 1 | 0.12 |
| Cooling Ingredient 2 | 0.06 |
| Optamint 188526 | 0.06 |
| Purified water | 82.61 |
| pH adjuster | 0.02 |
| Purified water | 0.18 |
| Total | 100.00 |

Example 9

Warming and Tingling Sensation

First and second compositions set forth below may be applied to a first and a second partner as set forth in Examples 1 and 2 above.

| Ingredient | % w/w |
|---|---|
| First Composition (Warming) | |
| Glycerin | 56.28 |
| Propylene Glycol | 40.00 |
| Maltodextrin | 2.50 |
| Honey | 1.00 |
| Methylparaben | 0.20 |
| Flavor | 0.02 |
| Total | 100.00 |
| Second Composition (Tingling) | |
| Propylene Glycol, USP | 15.00 |
| Natrosol 250H, NF | 0.75 |
| Benzoic Acid, USP | 0.20 |
| Polysorbate 60 | 1.00 |
| Cooling ingredient 1 | 0.06 |
| Optamint 188526 | 0.06 |
| Purified water I | 82.61 |
| Sodium hydroxide pellet* | 0.02 |
| Purified water II | 0.18 |
| Total | 100.00 |

Upon mixing, the compositions should result in a enhanced sensation that is warming plus tingling.

Example 10

The compositions and methods of this invention be used by couples to bring fun, excitement and playfulness to their intimate relationship. They may be characterized as a his/her interactive lubricant. The woman may apply to her skin one of the lubricants and will feel a slight sensation; the man should then apply to his skin another lubricant composition and will feel a slight sensation, when the two meet through intercourse a new and/or more intense warming sensation should be felt. The benefit is the fun and excitement of experiencing a new sensation together and the enhanced pleasure that comes from the warming sensation. Two combination technologies may be exemplified herein as follows:

Warming and tingling lubricants
Improved warming and water base lubricants

It is expected that the combined experience will be better than each individual experience, when intercourse begins (penetration) as well as, making the overall experience significantly better.

Delivery System

In view of the foregoing, it will be appreciated that the first and second compositions are to be contained in different containers, yet preferably used in conjunction with each other. In accordance with another aspect of this invention, a unique delivery system may be provided to enhance the experience provided by the compositions of this invention.

As may be readily appreciated, the provision of at least two different compositions warrants the provision of at least two containers, one for each composition. Moreover, because the compositions need not necessarily be used together and/or may be stored separately, it may be desirable to form the containers separately from each other so that users are not compelled to keep the containers together. Because the compositions are different, it is desirable to provide containers that may be distinguished from each other so that the compositions may be distinguished from each other. The containers may be substantially the same shape, but have other distinguishing features, such as different colors or different caps. Alternatively, the containers may be different shapes, but have certain shared features to signify the intended use of the compositions therein in conjunction with each other. For instance, containers that interlock, or have different shapes with similar graphics or logos, or other correlational features (such as shapes that are mirror images of each other) may be used. Interlocking or complementary shaped containers emphasize the complementary nature of the compositions to be contained therein and used in conjunction with each other.

The shape of the container may additionally, or alternatively, be influenced by the intended use of the composition to be contained therein and/or the intended message or other concepts to be conveyed by the invention. In the illustrative embodiment of FIGS. 1 and 3, an exemplary container 100 is shown in the shape of a vial, such as a test tube. Such shape may be desirable to convey the message of "experimentation," thus lending the fun and experimental concept of the invention. Also, an association between the test tube shape and the concept of mixing formulations to cause a chemical reaction resulting in a new and different formulation may be achieved by such container shape.

Figures 1, 2:
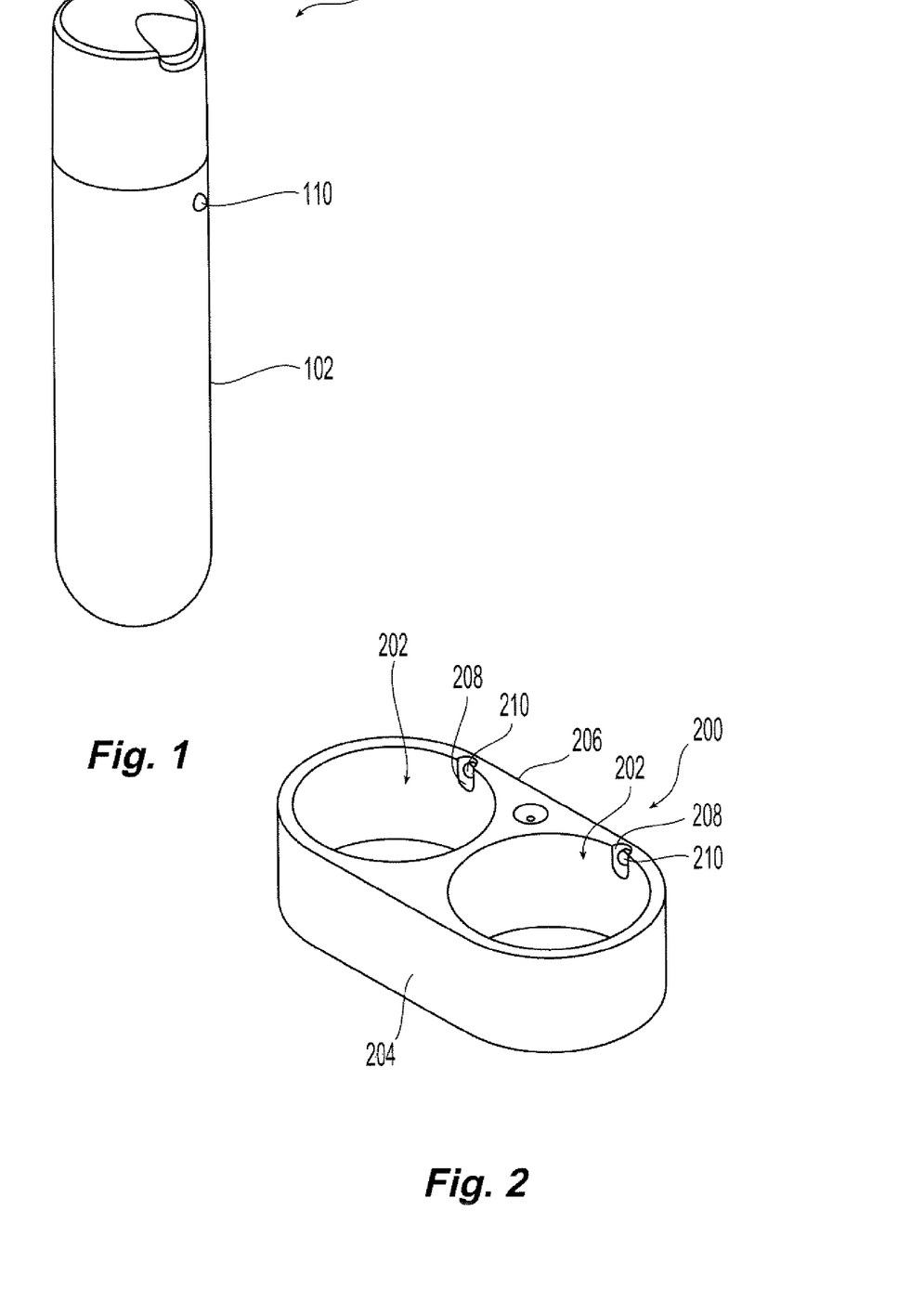
FIG. 1 is a perspective view of an exemplary container that may be used to contain a topical composition formed in accordance with the principles of the present invention.
FIG. 2 is a perspective view of an exemplary holder that may be used to link a pair of containers such as shown in FIG. 1.

Because the compositions to be held within exemplary containers 100 are intended to be used together, it may further be desirable to maintain the complementary containers 100 together by a connector element, such as a clip or a holder. The connector element may be designed to hold at least two containers together for use in conjunction with one another. An exemplary holder 200 is illustrated in FIG. 2 for holding a pair of containers 100 such as illustrated in FIG. 1. Thus, holder 200 is provided with two container-engaging sites 202, each shaped to engage a container 100 so that holder 200 may hold containers 100 together as a set. It will, however, be appreciated holder 200 need not be limited to two container-engaging sites 202. Thus, if more than two containers are intended to be included as a set, holder 200 may be provided with two or more container-engaging sites. Preferably, holder 200 is configured such that containers 100 may readily be coupled together and uncoupled multiple times without affecting the appearance and/or functionality of containers 100.

Figure 4:
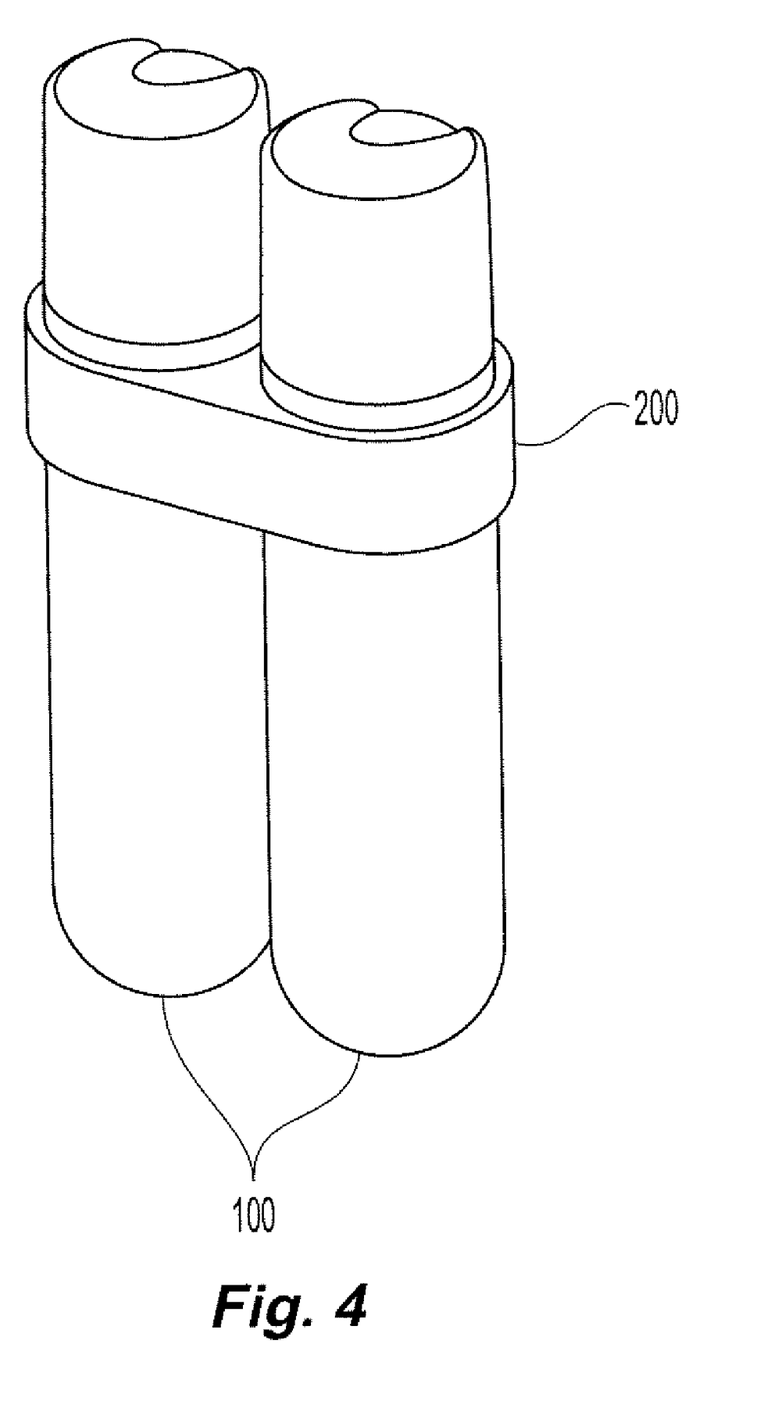
FIG. 4 is a perspective view of a pair of containers, such as shown in FIG. 1, linked by the exemplary holder of FIG. 2.

Holder 200 may be configured to be relatively compact. Additionally, holder 200 may be configured to facilitate ready storage of containers 100 such as in a purse or drawer. The simple ring or link configuration of exemplary holder 200 of FIGS. 2 and 4 achieve the desired function of holding at least two containers 200 together while also having a relatively low profile, thereby permitting ready storage or portability. For instance, holder 200 may be configured to permit ready storage in a substantially horizontal orientation, such as typical when storing in a drawer.

Figure 3:
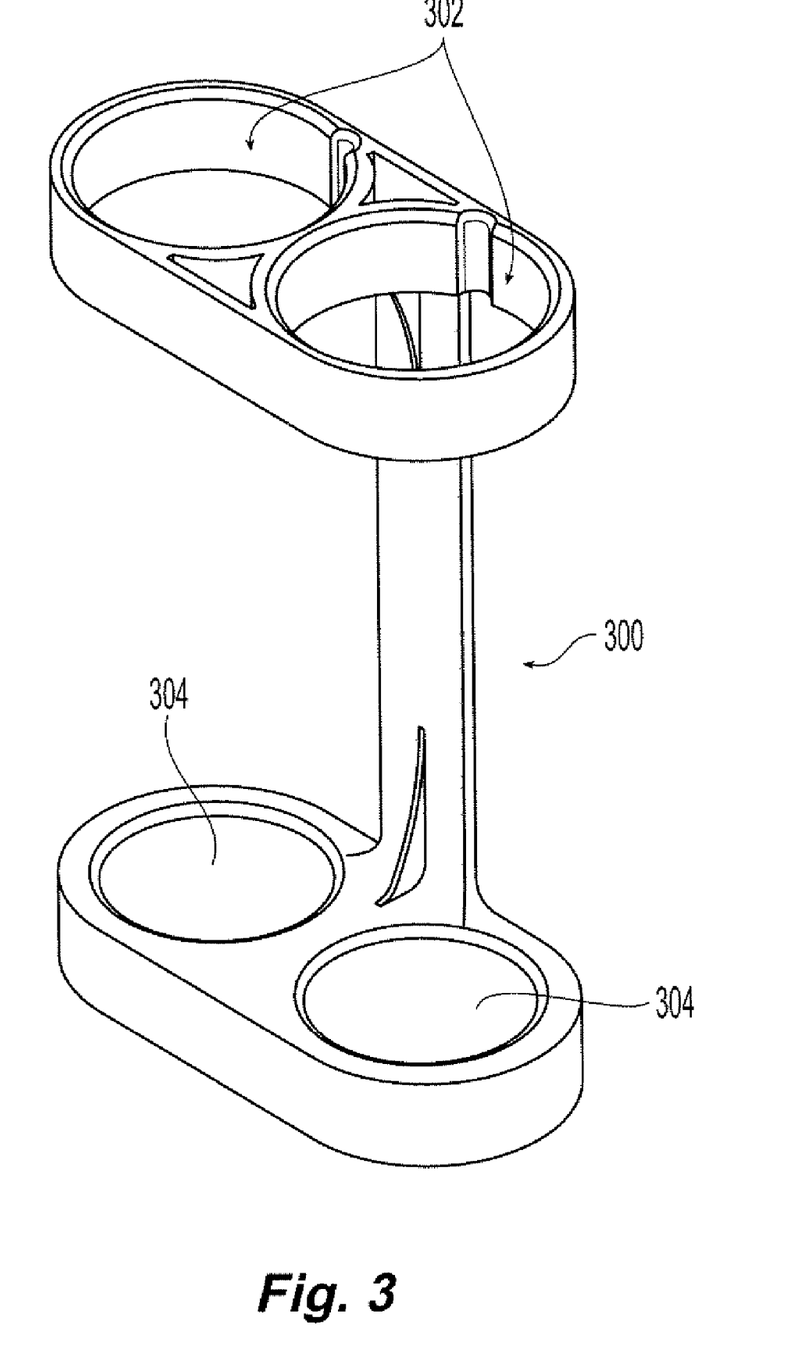
FIG. 3 is a perspective view of an alternate embodiment of a holder that may be used to link a pair of containers such as shown in FIG. 1.

The shape of containers 100 and/or holder 200 may be selected so as not to roll off a surface on which either is placed. For instance, holder 200 may have one or more walls, such as front wall 204 or back wall 206, with a substantially flat surface to provide stability when placed on a surface. Alternatively, or additionally, one or more containers 100 may be provided with a flat or protuberance (such as nub 110 described in further detail below) on container body 102 or cap 104 or both. However, a stand-type holder 300 may be used instead, such holder being reminiscent of test tube holders and thus further emphasizing the "experimentation" and "chemical reaction" messages that may be conveyed by the test-tube shaped vials. Stand-type holder 300 includes at least two container-engaging sites 302 as well as at least two corresponding container-supporting sites 304 on which the bottom ends of containers 100 may rest or be supported to maintain containers 100 in a substantially vertical orientation.

The above-described features for inhibiting containers 100 from rolling off a surface may serve an additional function of assisting engagement of containers 100 with holder 200. Of course, it will be appreciated that additional or completely separate features may be used, instead, to achieve such engagement. In the illustrative embodiment of FIGS. 1, 2, and 4, nubs 110 are provided on containers 100 to mate with recesses 208 in holder 200. If desired, a corresponding nub 210 may be provided in either or all of recesses 208 to further assure a stable and secure engagement of containers 100 in container-engaging sites 202 of holder 200. Similar features may be provided in alternate holder 300 as well. It will be appreciated that a reverse arrangement of nubs and recesses may be used. In other words, nubs may be provided in container-engaging sites 202 and corresponding recesses may be provided on container bodies 102. Other configurations of features assisting in engaging or securing containers 100 and holder 200 or 300 may be used without departing from the basic principles of the present invention. If desired, the features assisting in engaging or securing containers 100 and holder 200 may permit holder 200 to support container 100 independently. In other words, holding of only holder 200 permits a user to carry containers 100 without the need to actually hold containers 100. As such, portability of the delivery system comprising containers 100 and holder 200 is further enhanced.

The outer diameter of containers 100, the height of nubs 110, the inner diameter of container-engaging sites 202, the depth of recesses 208, and the height of nubs 210 (if provided) preferably are selected so that containers 100 are securely engaged within container engaging sites 202 of holder 200. Assurance of the desired dimensions and relative dimensions may be achieved in any of a variety of manners known to those of ordinary skill in the art. For instance, known manufacturing techniques may be used to assure the desired tolerances. More particularly, the manner of manufacturing either or both of containers 100 and holder 200 or 300 may be selected to assure high tolerances. In one embodiment, holder 200 may be formed by an injection molding process that permits tight tolerances to be maintained. Materials such as ABS (acrylonitrile butadiene styrene) or polypropylene are suitable for injection molding of holder 200. With such tight tolerances, containers 100 need not also be manufactured by methods that permit such high tolerances as well. Thus, for the sake of convenience, rapidity of manufacture, and cost-savings, containers 100 may be manufactured by extrusion blow-molding techniques. Materials such as PETG (polyethylene terephthalate glycol) may be used. The smallest outer diameter of containers 100 preferably is selected to be large enough for a friction fit within container-engaging sites 202 so that holder 200 securely holds containers 100.

Features for inhibiting containers 100 from rolling off a surface may serve yet another function of maintaining alignment of containers 100 during manufacturing and packaging of the delivery system of the present invention. Of course, it will be appreciated that additional or completely separate features may be used, instead, to achieve such alignment. Alignment of containers 100 during manufacture may be desired if the cap 104 is to be secured on container body 102 in a particular orientation, or if labels are to be applied in a particular orientation with respect to container body 102 or cap 104. Alignment of containers 100 may also be desirable with respect to holder 200 and/or secondary packaging for identification purpose, such as by aligning a label on container 100 to be visible when container 100 is held by holder 200 or displayed in a secondary packaging. If the alignment feature is in the form of a nub 110 as in the embodiment of FIG. 1, then it may be desirable to provide nub 110 in a position that would least interfere with interaction of container body 102 with another element, such as a label to be provided thereon.

While the foregoing description and drawings represent exemplary embodiments of a delivery system that may be used in conjunction with the formulations of the present invention, it will be understood that various additions, modifications and substitutions may be made therein without departing from the spirit and scope of the inventive delivery system. In particular, one skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the delivery system of the present invention being indicated by the appended claims, and not limited to the foregoing description thereof.

What is claimed is:

1. A delivery system for delivering first and second compositions formulated for application to different individuals and to interact with each other upon physical interactions of the individuals with each other, said delivery system comprising:
    a first container having a first cap;
    a first composition contained in said first container;
    a second container having a second cap, said second container and second cap being separable from said first container and first cap;
    a second composition contained in said second container;
    wherein:
    said second first composition, as applied on a first application site on a first individual, is formulated to interact with said first second composition, when said first composition is as applied to on a first second application site on a first second, different individual, and upon contact of said first composition on said first application site with said second composition is applied to a second application site on a second individual, and the application sites are contacted with each other on said second application site; and
    said first and second containers are associated with each other by at least one of color, shape, and physical connection to convey to the individuals that said first and second compositions contained respectively in said first and second containers are to be used in conjunction with each other.

2. A delivery system as in claim 1, wherein said first and second containers have substantially the same shape.

3. A delivery system as in claim 2, wherein said first and second containers are different colors.

4. A delivery system as in claim 2, wherein said first and second containers are test-tube shaped vials.

5. A delivery system as in claim 1, further comprising a holder configured to hold both said first and second containers together.

6. A delivery system as in claim 5, wherein:
    said first and second containers are in the shape of test-tube-shaped vials; and
    said holder has first and second container-engaging sites for engaging said first and second containers, respectively, to hold said first and second containers together.

7. A delivery system as in claim 6, wherein:
    said first and second containers each include at least one of a nub and a recess; and
    said first and second container-engaging sites of said holder each include at least one of a nub and a recess to interact with the at least one of a nub and a recess provided on each of said first and second containers to secure engagement of said first and second containers in said first and second container-engaging sites, respectively.

8. A delivery system as in claim 5, wherein said holder is configured to carry said first and second containers such that said holder independently supports said first and second containers.

9. A delivery system for delivering first and second compositions formulated for application to different individuals and to interact with each other upon physical interactions of the individuals with each other, said delivery system comprising:
    a first container containing a first composition;
    a second container containing a second composition formulated to interact with the first composition when the first and second compositions are applied to application sites on a first and second, individuals, respectively, and the application sites are contacted with each other; and a holder configured to couple said first and second containers together to convey to the individuals that said first composition and said second composition respectively contained in said first container and said second container are to be used in conjunction with each other;

wherein:

said first composition, as applied on a first application site on a first individual, is formulated to interact chemically with said second composition, as applied on a second application site on a second, different individual, upon contact of said first composition on said first application site with said second composition on said second application site;

said first and second containers are in the form of test-tube-shaped vials each having a separate cap, said vials each having side and bottom walls that are curved such that said vials can be rested on a support surface only in a horizontal orientation on said curved side walls;

said holder comprises first and second container-engaging sites configured (a) to engage said first and second containers, respectively, (b) to permit ready removal of at least one of said first and second containers from a respective container-engaging site for separate use of said first and second containers, and (c) to permit ready re-engagement of said at least one of said first and second containers in said respective container-engaging site; and said holder includes at least one wall with a substantially flat surface to provide stability when said holder, holding at least one of said first and second containers, is placed on a surface in a horizontal orientation.

10. A delivery system as in claim 9, wherein said at least one of a nub and a recess in each of said first and second containers and said first and second container-engaging sites of said holder are arranged to orient said first and second containers in a desired orientation with respect to said holder.

11. A delivery system as in claim 9, wherein said holder is configured to permit storage of said delivery system in a substantially horizontal orientation.

12. A delivery system as in claim 9, wherein said holder is configured to carry said first and second containers such that said holder independently supports said first and second containers.

* * * * *

UNITED STATES PATENT AND TRADEMARK OFFICE
CERTIFICATE OF CORRECTION

PATENT NO. : 7,726,487 B2  Page 1 of 1
APPLICATION NO. : 11/842271
DATED : June 1, 2010
INVENTOR(S) : Nawaz Ahmad et al.

It is certified that error appears in the above-identified patent and that said Letters Patent is hereby corrected as shown below:

Column 14, Line 14 delete "second";
Column 14, Line 16 delete "first" (first occurrence);
Column 14, Line 16 delete "when said first com-";
Column 14, Line 17 delete "position is";
Column 14, Line 17 delete "to";
Column 14, Line 17 delete "first";
Column 14, Line 18 delete "first";
Column 14, Line 18 delete "and";
Column 14, Line 20 delete "is applied to a second";
Column 14, Line 21 delete "application site on a second individual, and the applica-";
Column 14, Line 22 delete "tion sites are contacted with each other".

Column 14, Line 65, delete "for-";
Column 14, Line 66, delete "mulated to interact with the first composition when the";
Column 14, Line 67, delete "first and second compositions are applied to application";
Column 15, Line 1, delete "sites on a first and second, individuals, respectively, and";
Column 15, Line 2 delete "the application sites are contacted with each other".

Signed and Sealed this

Twenty-third Day of November, 2010

David J. Kappos
*Director of the United States Patent and Trademark Office*